United States Patent [19]

Hafner et al.

[11] Patent Number: 5,047,557

[45] Date of Patent: Sep. 10, 1991

[54] COMPLEXES HAVING OPTICALLY ACTIVE LIGANDS, A PROCESS FOR THEIR PREPARATION AND THEIR USE

[75] Inventors: Andreas Hafner, Frenkendorf; Rudolf Duthaler, Bettingen; Guido Bold, Gipf-Oberfrick, all of Switzerland

[73] Assignee: Ciba-Geigy Corporation, Ardsley, N.Y.

[21] Appl. No.: 481,416

[22] Filed: Feb. 16, 1990

[30] Foreign Application Priority Data

Mar. 8, 1989 [CH] Switzerland ............................ 867/89
Sep. 28, 1989 [CH] Switzerland ........................ 3511/89

[51] Int. Cl.$^5$ .............................................. C07F 00/00
[52] U.S. Cl. ........................................ 549/206; 549/4; 549/6; 549/209; 549/210; 549/214; 546/2; 546/6

[58] Field of Search ..................... 549/209, 214, 6, 4

[56] References Cited

U.S. PATENT DOCUMENTS 4,826,965   5/1989   Riediker et al. ................. 536/18.1

FOREIGN PATENT DOCUMENTS 90161   4/1989   Japan .

OTHER PUBLICATIONS

Narasaka et al., JACs, 1989; 111 pp. 5340–5345.
Narasaka et al. Chem. Letters; 2409–2412 (1987).
Narasaka et al., Chem. Letters; pp. 1109–1112 (1986).
Seebach et al., Chem. Abst. 108-203984v (1988).
Narasaka et al., Chem. Abst. 109-170279j (1988).
Narasaka et al. Chem. Abst. 111-57601m (1989).
Narasaka et al. Chem. Abst. 111-194322k (1989).
Helv. Chim. Acta. vol. 64; pp. 2485–2488 (1981).
Organometallics vol. 3; pp. 1716–1717 (1984).
Chem. Ber. vol. 118; pp. 3673–3682 (1985).

*Primary Examiner*—Cecilia Shen
*Attorney, Agent, or Firm*—Stephen V. O'Brien; JoAnn Villamizar

[57] ABSTRACT

Compounds of the formula I

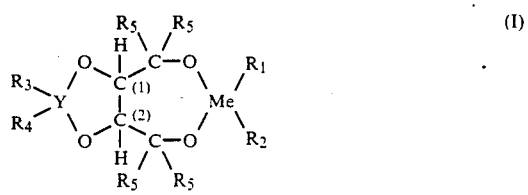

in which Me is Ti, Zr or Hf, $R_1$ is a group transferable to aldehyde, keto or imine groups, for example methyl, allyl, vinyl or the radical of an enol or enamine, $R_2$ is, for example, cyclopentadienyl, $R_3$ and $R_4$ are, for example, H or alkyl, $R_5$ is, for example, phenyl and the C(1) and C(2) atoms are chiral and have predominantly one configuration, are suitable for use as chiral reactants for aldehydes, ketones and imines for the preparation of both enantiomers of secondary or tertiary alcohols or tertiary amines.

18 Claims, No Drawings

COMPLEXES HAVING OPTICALLY ACTIVE LIGANDS, A PROCESS FOR THEIR PREPARATION AND THEIR USE

The invention relates to metal complexes having ligands of optically active 1,3-dioxolane-4,5-dimethanols, a radical which can be conferred to carbonyl groups or groups analogous to carbonyl and a cyclopentadienyl radical, to a process for their preparation and to their use as enantioselective reactants for aldehydes, ketones and N-substituted imines.

It is known from Helvetica Chimica Acta, volume 64, fasc. 7, No. 243, pages 2485-2488 (1981), Organometallics 3, pages 1716-1717 (1984) and Chem. Ber. 118, 3673-3682 (1985) that titanium compounds having a transferable group and a radical derived from a chiral monohydroxy or dihydroxy compound can be reacted with aldehydes to give secondary alcohols. Aliphatic chiral hydroxy compounds as ligands result in only moderate stereoselective conversions, whereas high optical yields can be achieved using chiral dinaphthol as the ligand. The chiral ligands used are difficult of access and expensive in industrial amounts.

EP-A 0,254,685 describes cyclopentadienyl-titanium complexes having optically active sugar ligands which produce chiral secondary alcohols at high enantioselective conversions in high yields when reacted with, for example, aldehydes. By virtue of the natural sugar ligands, it is, however, only possible to obtain one enantiomer of the alcohol.

There is a requirement for low-cost chiral organometallic reagents which are available in industrial quantities and have high stereoselective conversions when reacted with prochiral aldehydes, ketones and imines, in which the chiral ligand is derived from one of the pairs of enantiomers or diastereomers so that, for example, when reacted with aldehydes, a secondary alcohol having the R-configuration or the S-configuration can be prepared in a controlled manner.

The invention relates to compounds of the formula I

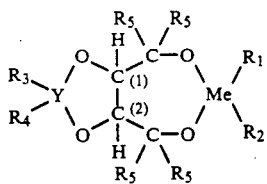

in which Me is tetravalent titanium, zirconium or hafnium, $R_1$ is linear or branched alkyl, alkenyl, alkynyl or cycloalkyl or cycloalkenyl each of which is unsubstituted or substituted by $C_1$-$C_4$alkyl, or is aryl, alkaryl, aralkyl, alkaralkyl, aralkenyl, alkaralkenyl, aralkynyl or alkaralkynyl each of which is unsubstituted or monosubstituted or polysubstituted by $(C_6H_5)_2P-$, $(R_6O)_2P(O)-$, $(R_6)_3Si-$, $(R_6)_3SiO-$, $R_6SO_2-$, $-S-C_2-C_4$alkylene-S- or $-O-C_2-C_4$alkylene-O- in which $R_6$ is phenyl, benzyl or $C_1$-$C_8$alkyl, cyano, F, nitro, $C_1$-$C_{12}$alkylthio, $C_1$-$C_{12}$alkoxy, secondary amino or $-COR_7$ in which $R_7$ is the radical of a monohydric alcohol; or $R_1$ is a radical of an enol, enamine or enhydrazine which is linked via the O atom or N atom; $R_2$ is cyclopentadienyl or indenyl each of which is unsubstituted or substituted by alkyl, alkenyl, alkoxy, cycloalkyl, aryl, aralkyl, trialkoxysilyl, trialkylsilyl, $R_6SO_2-$ or halogen, Y is C, Si or $-Si-O-SiR_3R_4-$; $R_3$ and $R_4$ independently of one another are H, linear or branched alkyl or alkenyl or cycloalkyl or cycloalkenyl each of which is unsubstituted or substituted by $C_1$-$C_4$alkyl, or are aryl, aralkyl, alkaryl, alkaralkyl, aralkenyl or alkaralkenyl, or $R_3$ and $R_4$ together are $-C_nH_{2n}-$ in which n is 3 to 7 and which is unsubstituted or substituted by $-CN$, $-F$, $-Cl$, $-Br$, nitro, $C_1$-$C_{12}$alkylthio or $C_1$-$C_{12}$alkoxy, $R_5$ is aryl, heteroaryl, aralkyl or heteroarylalkyl each of which is unsubstituted or substituted by $C_1$-$C_{12}$alkyl, $C_1$-$C_{12}$alkoxy, $C_1$-$C_{12}$alkylthio, cyano, secondary amino, secondary aminocarbonyl, fluorine, $C_6$-$C_{10}$aryl, $R_6SO_2-$, $C_1$-$C_{12}$alkoxymethyl, $C_1$-$C_{12}$alkylthiomethyl, secondary aminomethyl or secondary aminocarbonylmethyl, or is $C_1$-$C_{12}$alkyl, $C_2$-$C_{12}$alkenyl, $C_2$-$C_{12}$alkynyl, $C_3$-$C_8$cycloalkyl or $C_3$-$C_8$cycloalkenyl, and C(1) and C(2) are chiral C atoms, predominantly in the form of enantiomers or diastereomers.

If Y is a C atom, this can also be chiral, in which case diastereomers can be formed.

$R_1$ is a group which is transferable to carbonyl and imine compounds.

As alkyl, $R_1$ preferably contains 1 to 18, especially 1 to 12 and particularly 1 to 6, C atoms. Examples are methyl, ethyl, and the isomers of propyl, butyl, pentyl, hexyl, heptyl, octyl, nonyl, decyl, undecyl, dodecyl, tridecyl, tetradecyl, pentadecyl, hexadecyl, heptadecyl and octadecyl.

As alkenyl, $R_1$ preferably contains 2 to 12, especially 2 to 6, C atoms. It can be either alkenylalkyl of the formula $(C_nH_{2n-1})-C_mH_{2m}$ in which n is a number from 2 to 12, preferably 2 to 6, and m is a number from 1 to 6, preferably 1 or 2, or alkylvinyl which preferably has 1 to 10 C atoms in the alkyl group. Examples are: allyl, 1-methylallyl, 2-methylallyl, but-2-en-4-yl, but-1-en-3-yl, pent-3-en-5-yl, pent-1-en-3-yl, hex-4-en-6-yl, hex-2-en-4-yl, hept-2-en-1-yl, hept-3-en-5-yl, oct-6-en-8-yl, oct-2-en-4-yl, non-2-en-2-yl, dec-8-en-10-yl, dodec-3-en-12-yl, vinyl, crotonyl, n-but-1-en-1-yl, but-2-en-3-yl, pent-1-en-2-yl and hex-1-en-1-yl. $R_1$ is preferably vinyl or allyl. It is particularly preferable for $R_1$ to be allyl.

As alkynyl, $R_1$ preferably contains 2 to 12, especially 2 to 6, C atoms. The alkynyl group can either be located in the carbon chain or can be terminal. Examples are: ethynyl, prop-2-yn-3-yl, pent-2-yn-4-yl, pent-1-yn-5-yl and hex-1-yn-6-yl. Ethynyl and propargyl are preferred.

As cycloalkyl or cycloalkenyl, $R_1$ preferably contains 3 to 8, especially 3 to 6 and particularly 5 or 6, ring C atoms and these can be substituted by $C_1$-$C_4$alkyl. Examples are cyclopropyl, cyclobutyl, cyclopentyl, cyclohexyl, cycloheptyl, cyclooctyl, cyclodecyl, cyclododecyl, cyclopropenyl, cyclobutenyl, cyclopent-1-en-3-yl, cyclopent-1-en-1-yl, cyclohex-1-en-3-yl, cyclohex-2-en-1-yl, cyclohept-1-en-3-yl, cyclooct-1-en-3-yl and 4-methylcyclohex-1-en-3-yl.

As aryl, $R_1$ preferably contains 6 to 12 C atoms and is preferably naphthyl and especially phenyl.

As alkaryl, $R_1$ preferably contains 7 to 16 C atoms. The aryl is preferably phenyl. Examples are: methylphenyl, dimethylphenyl, ethylphenyl, n-propylphenyl, isopropylphenyl, n-, iso- and t-butylphenyl, di-t-butylphenyl, hexylphenyl, octylphenyl and decylphenyl.

As aralkyl, $R_1$ preferably contains 7 to 16, especially 7 to 10, C atoms. The aryl in this is preferably phenyl. Examples are: benzyl, 1-phenylethyl, 2-phenylethyl, 1-phenylpropyl, 2-phenylpropyl, phenylbutyl, phenyl-pentyl and phenylhexyl. Benzyl and 1-phenylethyl or 2-phenylethyl are preferred.

As alkaralkyl, $R_1$ can preferably contain 8 to 16 C atoms. The aryl in this is preferably phenyl. Examples are: methylbenzyl, ethylbenzyl, n-propylbenzyl, isopropylbenzyl, dimethylbenzyl, n-, iso- or t-butylbenzyl, di-t-butylbenzyl, hexylbenzyl, nonylbenzyl, 1-methylphenyleth-2-yl, 2-methylphenyleth-2-yl and 1-methylphenylprop-3-yl.

As aralkenyl, $R_1$ preferably contains 8 to 16 C atoms. The aryl in this is preferably phenyl. Examples are: phenylvinyl, 1-phenylprop-1-en-3-yl, 2-phenylprop-2-en-1-yl, 3-phenylprop-1-en-3-yl, phenylbutenyl, phenylpentenyl or phenylhexenyl.

As alkaralkenyl, $R_1$ preferably contains 9 to 16 C atoms. The aryl in this is preferably phenyl. Examples are: methylphenylvinyl, ethylphenylvinyl, dimethylphenylvinyl, 1-methylphenylprop-2-en-3-yl and 2-methylphenylprop-2-en-3-yl.

As aralkynyl, $R_1$ preferably contains 8 to 16 C atoms. The aryl in this is preferably phenyl. Examples are: phenylethynyl, phenylpropynyl and 1-phenylbut-3-yn-4-yl.

As alkaralkynyl, $R_1$ preferably contains 9 to 16 C atoms. The aryl in this is preferably phenyl. Examples are: methylphenylethynyl and methylphenylpropargyl.

Some examples of radicals $R_1$ are $-CH_2P(O)(OR_6)_2$, methyl, ethyl, vinyl, allyl, crotyl and substituted allyl radicals, for example $-CH_2CH=CH-P(C_6H_5)$, $-CH(SO_2R_6)CH=CH-Si(R_6)_3$,

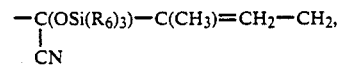

$-CH=CH-SO_2-R_6$, $-CH_2-CH=CH-OR'$ and

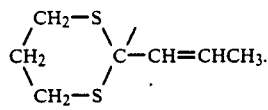

$R_6$ can be as defined above. Examples of $R'$ can be $C_1-C_8$alkyl or $-Si(R_6)_3$.

The enol radical $R_1$ is attached to the metal Me via the enol oxygen atom. Linear or cyclic enols are possible. The enol radical $R_1$ preferably contains up to 20, particularly 2 to 16, C atoms. The cyclic enols can contain 3 to 8, particularly 4 to 6, ring atoms, it being possible for the ring to be formed from atoms of the group comprising C, O, S and N. The enol radical $R_1$ can, for example, have the general formula

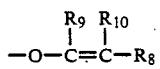

$R_9$ can, for example, be H or substituted or unsubstituted $C_1-C_8$alkyl, $C_1-C_8$alkoxy, $C_1-C_8$alkylthio, cycloalkyl having 3 to 6 ring C atoms, phenyl, benzyl, phenoxy, phenylthio, benzyloxy, benzylthio, secondary amino, $-OB(OC_1-C_8-alkyl)_2$, $-OSn(R_{11})_3$ in which $R_{11}$ is $C_1-C_8$alkyl, phenyl or benzyl, $-OTi(R_{11})_3$, $-OLi$ or $-OSi(R_6)_3$. $R_{10}$ and $R_8$ independently can be H, F or substituted or unsubstituted $C_1-C_8$alkyl, $C_1-C_8$alkoxy, $C_1-C_8$alkylthio, cycloalkyl having 3 to 6 ring C atoms, phenyl, benzyl, phenoxy, phenylthio, benzyloxy, benzylthio, secondary amino or $-OSi(R_6)_3$.

Suitable substituents for $R_9$ are the substituents mentioned for $R_1$. The secondary amino group can contain $C_1-C_8$alkyl groups, phenyl, benzyl or $(R_6)_3Si$ groups. Secondary amino groups preferably containing 4 to 6 ring atoms from the group comprising C, O, S, Si and N are also possible. $R_9$ and $R_{10}$ or $R_{10}$ and $R_8$, respectively, together with the C atoms to which they are attached, can form a 3-membered to 8-membered, preferably 4-membered to 6-membered, carbocyclic or heterocyclic ring, it being possible for the heterocyclic ring to contain atoms from the group comprising C, O, S and N. The rings can be substituted as defined above for $R_1$. A preferred group is formed by ester-enolates in which $R_9$ is $C_1-C_8$alkoxy. Another preferred group is formed by enols of glycine derivatives which, for example, have the formula

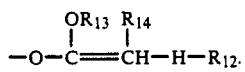

$R_{13}$ can, for example, be benzyl, phenyl or $C_1-C_8$alkyl. $R_{14}$ and $R_{12}$ can be $C_1-C_8$alkyl, phenyl or benzyl, or they can, together with the N atom, form a heterocyclic structure which can contain further heteroatoms from the group comprising O, S or N. $R_{13}$ and $R_{14}$ together can also be methylene or ethylene. $R_{14}$ and $R_{12}$ can also be detachable protective groups, for example $(R_6)_3Si-$ or $-Si(R_6)_2CH_2CH_2Si(R_6)_2-$. $R_{13}$, $R_{14}$ and $R_{12}$ can be substituted as defined above for $R_1$. Another preferred group is formed by enol radicals of the formula

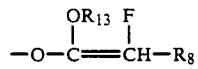

in which $R_8$ and $R_{13}$ are as defined above.

$R_1$ can also be the radical of an enamine or enhydrazine each of which is attached to the metal Me via an N atom. Linear or cyclic enamines or enhydrazines preferably containing up to 20, particularly 2 to 16, C atoms are possible. The cyclic enamines and enhydrazines can contain 3 to 8, particularly 4 to 6, ring atoms, it being possible for the ring to be formed from atoms of the group comprising C, O, S and N. The N atom of the enamine group can be substituted, preferably by $C_1-C_8$alkyl, phenyl, benzyl or protective groups, for example $(R_6)_3Si-$.

The enamine radical or enhydrazine radical can, for example, have the formula

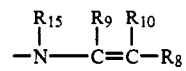

in which $R_9$, $R_{10}$ and $R_8$ are as defined above for the enol radical $R_1$, $R_9$ and $R_{15}$, together with the C—N—group, or $R_{10}$ and $R_{15}$, together with the —N—C═C— group, form a 3-membered to 8-membered, preferably 4-membered to 6-membered, heterocyclic structure which can contain further heteroatoms from the group comprising O, S and N, and $R_{15}$ is H, $C_1-C_8$alkyl, phenyl, benzyl, $C_1-C_8$alkoxy, phenoxy, benzyloxy, $(R_6)_3Si-$ or $-NR_{16}R_{17}$ in which $R_6$ is as defined above and $R_{16}$ and $R_{17}$ are H, $C_1-C_8$alkyl, phenyl or benzyl. In a preferred group $R_9$ is H, $C_1-C_8$alkyl or phenyl and $R_{10}$ and $R_8$ are H. The enol, enamine and enhydrazine radicals are C-nucleophiles capable of aldol reactions.

As the radical of an enol, $R_1$ can also be a ketone-enolate containing, in particular, up to 16 C atoms, especially 4 to 16 C atoms. These enolates can be derived from β-ketoaldehydes, 1,3-diketones, β-ketocarboxylic acid esters and β-ketocarboxamides. The ester group preferably contains radicals of aliphatic $C_1$-$C_6$alcohols. The N atom in the amide group can be monosubstituted or disubstituted, preferably by $C_1$-$C_6$alkyl. The following are examples: β-ketobutyraldehyde, acetylacetone, benzoyl acetone, ethyl acetoacetate and acetoacetamide.

The radical $R_1$ can be monosubstituted or polysubstituted, preferably monosubstituted to trisubstituted and particularly monosubstituted or disubstituted. If the substituent is alkoxy or alkylthio, it preferably contains 1 to 6 C atoms. $R_7$ is preferably the radical of an aliphatic alcohol having 1 to 6 C atoms. Possible examples are radicals of aliphatic or cycloaliphatic alcohols. The following are examples: methoxy, ethoxy, n-propoxy, isopropoxy, n-, iso- and t-butoxy, pentoxy, hexyloxy, cyclopentyloxy and cyclohexyloxy.

As alkyl, $R_6$ preferably contains 1 to 6 C atoms, particularly 1 to 4 C atoms. The alkoxy, alkylthio, -S-$C_2$-$C_4$alkylene-S- and -O-$C_2$-$C_4$alkylene-O- groups can be attached to a C atom; they are then acetal or ketal groups.

When it is a substituent, the secondary amino can have the formula —$NR_{18}R_{19}$ in which $R_{18}$ and $R_{19}$ are $C_1$-$C_{12}$alkyl, preferably $C_1$-$C_6$alkyl, cyclopentyl, cyclohexyl, phenyl, benzyl or $(R_6)_3Si$, or $R_{18}$ and $R_{19}$ together are $C_3$-$C_6$alkylene, 3-oxapentylene or -Si$(R_6)_2$-$C_2$-$C_3$alkylene-Si$(R_6)_2$- and $R_6$ is as defined above.

In a preferred subgroup $R_1$ is linear or branched $C_1$-$C_{12}$alkyl, $C_2$-$C_{12}$alkenyl, $C_2$-$C_{12}$alkynyl, cycloalkyl or cycloalkenyl each of which has 3 to 8 ring C atoms, $C_6$-$C_{12}$aryl, $C_7$-$C_{16}$alkaryl, $C_7$-$C_{16}$aralkyl, $C_8$-$C_{16}$alkaralkyl, $C_8$-$C_{16}$aralkenyl, $C_9$-$C_{16}$alkaralkenyl, $C_8$-$C_{16}$aralkynyl or $C_9$-$C_{16}$alkaralkynyl each of which is unsubstituted or monosubstituted or polysubstituted by secondary amino, cyano, nitro, $C_1$-$C_6$alkylthio, $C_1$-$C_6$alkoxy or —$COR_7$ in which $R_7$ is $C_1$-$C_{12}$alkoxy; or $R_1$ is a radical of an enol, enamine or enhydrazine which is attached via the enol oxygen atom or via the enamine nitrogen atom.

In another preferred subgroup $R_1$ is linear or branched $C_1$-$C_6$alkyl, $C_2$-$C_6$alkenyl, $C_2$-$C_6$alkynyl, cycloalkyl or cycloalkenyl each of which has 3 to 6 ring C atoms, phenyl, ($C_1$-$C_{10}$alkyl)-phenyl, phenyl-($C_1$-$C_2$alkyl), ($C_1$-$C_8$alkyl)-phenyl-($C_1$-$C_2$alkyl), phenylvinyl, phenylethynyl or phenylpropargyl, ($C_1$-$C_8$alkyl)-phenylvinyl, ($C_1$-$C_8$alkyl)-phenylethynyl or ($C_1$-$C_7$alkyl)-phenylpropargyl each of which is unsubstituted or monosubstituted or polysubstituted by secondary amino, cyano, nitro, $C_1$-$C_6$alkoxy, $C_1$-$C_6$alkylthio or —$COR_7$ in which $R_7$ is $C_1$-$C_{12}$alkoxy; or $R_1$ is a radical of an enol, enamine or enhydrazine which has up to 20 C atoms and is attached via an enol oxygen atom or an enamine nitrogen atom.

It is particularly preferable for $R_1$ to be methyl, ethyl, vinyl, allyl, crotonyl, ethynyl, propargyl, cyclopentyl, cyclohexyl, cyclopentenyl, cyclohexenyl, phenyl, methylphenyl, benzyl, 1-phenyleth-2-yl, methylbenzyl, phenylvinyl, methylphenylvinyl, phenylethynyl, phenylpropargyl, methylphenylethynyl, dimethylphenylethynyl or dimethylphenylpropargyl each of which is unsubstituted or monosubstituted or polysubstituted by secondary amino, cyano, nitro, $C_1$-$C_6$alkoxy, $C_1$-$C_6$alkylthio or —$COR_7$ in which $R_7$ is $C_1$-$C_{12}$alkoxy; or $R_1$ is a radical of an enol, enamine or enhydrazine which has 2 to 16 C atoms and is attached via the enol oxygen atom or via the enamino nitrogen atom.

In particular $R_1$ is methyl, ethyl, allyl or the radical of an ester-enolate which can be substituted by secondary amino.

When $R_2$ is cyclopentadienyl or indenyl, it can be substituted, for example by 1 to 5, for example 1 or 2, substituents. Examples of suitable substituents are alkyl preferably having 1 to 6 C atoms, alkenyl preferably having 2 to 6 C atoms, alkoxy preferably having 1 to 6 C atoms, cycloalkyl preferably having 5 or 6 ring C atoms, aryl preferably having 6 to 12 C atoms, aralkyl preferably having 7 to 13 C atoms, trialkoxysilyl preferably having 1 to 6 C atoms in the alkoxy groups, trialkylsilyl preferably having 1 to 6 C atoms in the alkyl groups, halogen, preferably F, Cl or Br, or $R_6$—$SO_2$— in which $R_6$ is preferably phenyl, tolyl, benzyl or $C_1$-$C_6$alkyl. Aryl is especially phenyl and aralkyl is especially benzyl.

If Me is titanium, $R_2$ as cyclopentadienyl or indenyl preferably contains no substituents or 1 to 5 substituents, particularly 1, 2 or 3. If Me is zirconium or hafnium, $R_2$ as cyclopentadienyl or indenyl preferably contains 3 to 5 substituents, particularly methyl or trialkylsilyl groups.

In a preferred embodiment $R_2$ is cyclopentadienyl or indenyl which is unsubstituted or substitued by $C_1$-$C_6$alkyl, $C_2$-$C_6$alkenyl, $C_1$-$C_6$alkoxy, cycloalkyl having 5 or 6 ring C atoms, phenyl, benzyl, trialkoxysilyl having 1 to 6 C atoms in the alkoxy groups, trialkylsilyl having 1 to 6 C atoms in the alkyl groups, F, Cl, Br or $R_6SO_2$—.

In another preferred embodiment $R_2$ is cyclopentadienyl which is unsubstituted or substituted by $C_1$-$C_6$alkyl or trimethylsilyl.

It is particularly preferable for $R_2$ to be cyclopentadienyl, pentamethylcyclopentadienyl, trimethylsilylcyclopentadienyl, bis-(trimethylsilyl)-cyclopentadienyl or tris-(trimethylsilyl)-cyclopentadienyl.

The same preferences as for $R_1$ apply to $R_3$ and $R_4$ when they are hydrocarbon radicals.

Examples of $R_1$ have been enumerated. As alkyl, $R_3$ and $R_4$ preferably contain 1 to 18, especially 1 to 12 and particularly 1 to 6, C atoms. The following are examples: methyl, ethyl, n-propyl, isopropyl, n-, iso- or t-butyl, pentyl, hexyl, heptyl, octyl, nonyl, decyl, undecyl, dodecyl, tetradecyl, hexadecyl, octadecyl and eicosyl. Methyl, ethyl, propyl and butyl are particularly preferred. As cycloalkyl, $R_3$ and $R_4$ preferably contain 5 or 6 ring C atoms. Examples are cyclopentyl, cyclohexyl and methylcyclohexyl. When together as the group —$C_nH_{2n}$—, $R_3$ and $R_4$ are linear or branched alkylene having 3 to 7, preferably 4 to 6, C atoms in the alkylene group. Substituents for $R_3$ and $R_4$ which are particularly preferred are —F, —Cl, $C_1$-$C_6$alkylthio or $C_1$-$C_6$alkoxy.

In a preferred embodiment $R_3$ and $R_4$ independently of one another are H, $C_1$-$C_{12}$alkyl, $C_2$-$C_{12}$alkenyl, cycloalkyl or cycloalkenyl each of which has 5 or 6 ring C atoms and is unsubstituted or substituted by $C_1$-$C_4$alkyl, or are phenyl, naphthyl, benzyl, $C_1$-$C_6$alkylphenyl or $C_1$-$C_6$alkylbenzyl, or $R_3$ and $R_4$ together are —$C_nH_{2n}$— in which n is 4 to 6, these groups being unsubstituted or substituted by —CN, —F, —Cl, nitro, $C_1$-$C_6$alkylthio or $C_1$-$C_6$alkoxy.

In another preferred embodiment $R_3$ and $R_4$ independently of one another are H, $C_1$-$C_6$alkyl, for example methyl, ethyl, propyl and butyl, cyclopentyl or cyclohexyl each of which is unsubstituted or substituted by $C_1$–$C_4$alkyl, or are phenyl, benzyl, $C_1$–$C_6$alkylphenyl or $C_1$–$C_6$alkylbenzyl, or $R_3$ and $R_4$ together are pentamethylene or tetramethylene.

A preferred subgroup is formed by compounds in which $R_3$ is H and $R_4$, or $R_3$ and $R_4$, are one of the hydrocarbon radicals defined above.

Y in formula I is especially C. If this C atom is chiral, the compounds of the formula I embrace diastereomers. $R_3R_4Y$ can be $R_3R_4Si$ in which $R_3$ and $R_4$ are preferably $C_1$–$C_6$alkyl, especially $C_1$–$C_4$alkyl. $R_3R_4Y$ can also be —$SiR_3R_4$—O—$SiR_3R_4$— in which $R_3$ and $R_4$ are preferably $C_1$–$C_4$alkyl.

As aryl, $R_5$ is preferably $C_6$–$C_{10}$aryl and is especially phenyl or naphthyl. As heteroaryl, $R_5$ is preferably 5-membered or 6-membered heteroaryl having a heteroatom from the group comprising O, S and N. As aralkyl, $R_5$ is preferably benzyl or naphthylmethyl and heteroarylmethyl in which the heteroaryl contains 5 or 6 ring members and heteroatoms from the group comprising O, S and N. Examples of heteroaryl are pyridyl, furyl, thiophenyl and pyrryl. The substituents alkyl, alkoxy and alkylthio preferably contain 1 to 6 C atoms. Secondary amino is preferably di-($C_1$–$C_4$alkyl)-amino. Secondary aminocarbonyl is especially di-($C_1$–$C_4$alkylamino)-carbonyl. The same preferences apply to the correspondingly substituted methyl radicals as substituents.

As alkyl, alkenyl and alkynyl, $R_5$ can follow the preferences indicated for $R_1$.

$R_5$ is preferably $C_2$–$C_4$alkenyl, 2-furyl or $C_6$–$C_{10}$aryl each of which is unsubstituted or substituted by $C_1$–$C_6$alkyl or F. Aryl is preferably methylphenyl, pentafluorophenyl, phenyl or naphthyl. $R_5$ is especially propenyl, phenyl, pentafluorophenyl, methylphenyl or furyl.

A preferred embodiment is constituted by compounds of the formula I in which $R_1$ is linear or branched $C_1$–$C_4$alkyl, $C_2$–$C_6$alkenyl or cycloalkyl or cycloalkenyl each of which has 3 to 6 ring C atoms and is unsubstituted or substituted by $C_1$–$C_4$alkyl, or $R_1$ is phenyl, benzyl, $C_1$–$C_6$alkylphenyl or $C_1$–$C_6$alkylbenzyl each of which is unsubstituted or substituted by secondary amino, cyano, nitro, $C_1$–$C_6$alkoxy, $C_1$–$C_6$alkylthio or —$COR_7$ in which $R_7$ is $C_1$–$C_{12}$alkoxy, or $R_1$ is a radical of an enol, enamine or enhydrazine which has up to 12 C atoms and is attached via an enol oxygen atom or an enamino nitrogen atom, $R_2$ is cyclopentadienyl which is unsubstituted or substituted by $C_1$–$C_4$alkyl or trimethylsilyl, Y is C, $R_3$ is H or is as defined for $R_4$ and $R_4$ is $C_1$–$C_{12}$alkyl, phenyl, benzyl, cyclopentyl or cyclohexyl or $R_3$ and $R_4$ together are tetramethylene or pentamethylene, $R_5$ is $C_2$–$C_4$alkenyl, phenyl, pentafluorophenyl or furyl and Me is tetravalent titanium, zirconium or hafnium.

The C(1) and C(2) atoms in formula I preferably have the R,R- or S,S-configuration. If Y in formula I is a chiral C atom, the C(1) and C(2) atoms can also have the R,S- or S,R-configuration.

A particularly preferred embodiment is constituted by compounds of the formula I in which $R_1$ is $C_1$–$C_4$alkyl, allyl or the radical of an ester-enolate which has 2 to 12 C atoms and can be substituted by secondary amino, $R_2$ is cyclopentadienyl which is unsubstituted or substituted by methyl or trimethylsilyl, $R_3$ is H or is as defined for $R_4$ and $R_4$ is $C_1$–$C_6$alkyl, $R_5$ is propenyl, phenyl, pentafluorophenyl or furyl and Me is tetravalent titanium, zirconium or hafnium and Y is C.

The compounds of the formula I can be prepared by reacting a compound of the formula II

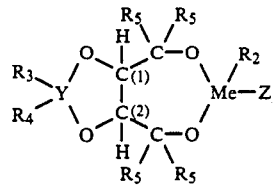

with a compound of the formula III

in the presence of an inert solvent and an inert protective gas, $R_1$, $R_2$, $R_3$, $R_4$, $R_5$, Me and Y being as defined above, Z being an anion and $M^\oplus$ being $Li^\oplus$, $Na^\oplus$, $K^\oplus$, $MgX^\oplus$, $ZnX^\oplus$, $CdX^\oplus$, $HgX^\oplus$, $CuX^\oplus$ or quaternary ammonium, X being halogen.

In the group $M^\oplus$ of the formula III X is preferably Cl, Br or I. $M^\oplus$ is preferably $Li^\oplus$, $MgCl^\oplus$, $MgBr^\oplus$, $ZnCl^\oplus$, $ZnBr^\oplus$, $CdCl^\oplus$, $CdBr^\oplus$ or tetraalkylammonium having 1 to 6 C atoms in the alkyl groups. It is particularly preferable for $M^\oplus$ to be $MgX^\oplus$ and $Li^\oplus$, in which X is Cl, Br or I.

Examples of suitable anions Z are $PF_6^\ominus$—, $SbF_6^\ominus$—, $BF_4^\ominus$—, $CF_3COO^\ominus$, sulfonate (for example tosylate) and particularly $Cl^\ominus$ or $Br^\ominus$.

The invention also relates to the compounds of the formula II. They are obtainable in a simple manner by reacting 1 mole of a salt of the formula

with 1 mole of a compound of the formula IV

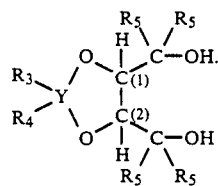

The compounds of the formula IV can be prepared from correspondingly optically active tartaric acid esters protected with a group $R_3R_4Y<$ by means of Li-organic compounds or Grignard reagents, for example of the formula $R_5Li$ or $R_5MgX$ in which X is Cl, Br or I. The preparation is described by D. Seebach et al. in Helv. Chim. Acta 70, page 954 (1987).

The reaction can be carried out at temperatures from $-78°$ to $+100°$ C., preferably $-20°$ to $40°$ C., preferably in an inert solvent, for example hydrocarbons (toluene or xylene) or ethers (diethyl ether, tetrahydrofuran, dioxane or ethylene glycol dimethyl ether). The reaction is preferably carried out under an atmosphere of a protective gas, for example argon, and in the presence of a basic compound, in order to bind the HZ formed. Examples of suitable basic compounds are alkali metal carbonates, such as sodium carbonate and bicarbonate, and also amines, particularly tertiary amines, for example triethylamine. Other suitable bases are LiH, KH, NaH, lithium secondary amides (lithium diisopropylamide), methyllithium, ethyllithium, lithium hexamethyldisilazide, sodium hexamethyldisilazide, potassium hexamethyldisilazide, methylmagnesium chloride or diethylzinc. The reaction solution can be used for the next stage without further treatment. The compounds are isolated by filtering off the precipitated salt and removing the solvent. The crude products thus obtained can be used for the next stage without purification.

The preparation of the compounds of the formula I is preferably effected at temperatures from −78° to +40° C., preferably −20° to 40° C., and in an inert solvent. Suitable solvents are, in particular, ether. The reaction is carried out under a protective gas, for example argon. Precipitated salts can be filtered off. The resulting crude product, if appropriate after removal of the solvent, can be used for the next stage without further treatment.

The compounds according to the invention are excellently suitable for use as enantioselective reactants for reactions with prochiral aldehyde, keto and/or N-substituted imine groups. It is a particular advantage that, depending on the choice of the R,R- or S,S-configuration at the C atoms C(1) and C(2) in formula I, both enantiomers can be prepared. They are particularly suitable for the transfer of allyl groups, and also enol, enamine and enhydrazine groups, by the aldol reaction. The invention also relates to this use. The carbonyl compounds are preferably prochiral aldehydes and ketones. The reaction products obtained, in high yields, are chiral, secondary or tertiary alcohols or secondary amines or aminoacids, with a high excess of one enantiomer. The synthesis of chiral active compounds in the field of pharmaceuticals and agricultural chemicals has become of great importance. The compounds according to the invention are suitable for the preparation of corresponding intermediates for the synthesis of such active compounds or for the introduction of groups having chiral C atoms in the final stage of the synthesis of active compounds of this type. Thus it is possible, for example, to prepare, in high yields, pheromones for the control of insects. An example which may be mentioned is (+)-ipsenol or (−)-ipsenol, which can be prepared by the process described in EP-A 0,254,685 using a titanium complex according to the invention (see Example 17).

In addition, the compounds according to the invention can be prepared at a low cost from cheap starting materials. As derivatives of natural compounds they can be disposed of in a manner not harmful to the environment by means of biological methods of degradation, especially as titanium or titanium oxide is, as is known, physiologically acceptable.

The present invention also relates to a process for the preparation of, preferably chiral, secondary and tertiary alcohols and secondary amines, which comprises reacting, preferably prochiral, aldehydes, ketones or N-substituted aldimines or ketimines with 1 mole of a compound of the formula I per mole of aldehyde, keto or imine group. The substituent in the imine can be the radicals previously mentioned, such as alkyl, alkenyl, cycloalkyl, aryl and aralkyl. If these radicals are substituted by carboxyl or carboxylic ester groups, the reaction products obtained are aminoacids or esters thereof, respectively. Examples of other suitable substituents are $R_6SO_2-$ and acyl which preferably has 1 to 8 C atoms and can be substituted by —F. Examples are acetyl, mono-, di- and tri-fluoroacetyl, benzoyl and fluorobenzoyl.

The reaction is advantageously carried out at temperatures from −80° to 30° C. in the presence of an inert solvent and under a protective gas. The reaction product is preferably isolated by hydrolysis, extracting the product and purifying it in a customary manner. Examples of suitable inert solvents are ethers or hydrocarbons, such as pentane, hexane, cyclohexane, methylcyclohexane, benzene, toluene, xylene, diethyl ether, tetrahydrofuran or dioxane, nitriles, for example acetonitrile, or chlorinated hydrocarbons, for example methylene chloride, chloroform or chlorobenzene.

The following examples illustrate the invention. Cp stands for cyclopentadienyl.

A) PREPARATION EXAMPLES

Example 1 a)

[(4S,5S)-2-(t-Butyl)-1,3-dioxolane-4,5-bis-(diphenylmethoxy)]yclopentadienyltitanium chloride 1.24 g (2.5 mmol) of (4S,5S)-2-(t-butyl)-4,5-[bis-(diphenylhydroxymethyl)]-1,3-dioxolane are added to a solution of 0.55 g (2.5 mmol) of cyclopentadienyltitanium trichloride in 50 ml of diethyl ether. A solution of 0.56 g (5.5 mmol) of triethylamine in 10 ml of diethyl ether is added dropwise in the course of 30 minutes and at room temperature (RT) to the reaction solution above. The pale yellow suspension is stirred for a further 12 hours at RT and the triethylamine hydrochloride formed is filtered off with suction under argon and washed with three times 10 ml of ether. The reaction solution thus obtained can be used for the next stage without further treatment. The complex is isolated by removing the solvent by vacuum distillation. Two diastereomers are formed in a ratio of 4:1.

Main Isomer $^1$H-NMR spectrum ($CD_2Cl_2$, 400 MHz): 7.20–7.70 (m, 20H, Ph); 6.26 (s, 5H, Cp); 4.86 (d, J=6.5 1H, H-C(4) or H-C(5)); 4.79 (d, J=6.5, 1H, H-(C5) or H-C(4)); 3.43 (s, 1H, H-C(2)); 0.84 (s, 9H, C($\underline{CH_3}$)$_3$).

$^{13}$C-NMR spectrum ($CD_2Cl_2$, 100 MHz): 147.22 (s, Ph); 146.79 (s, Ph); 142.83 (s, Ph); 142.17 (s, Ph); 128.73 (d, Ph); 128.59 (d, Ph); 128.24 (d, Ph); 128.08 (d, Ph); 172.99 (d, Ph); 127.92 (d, Ph); 127.91 (d, Ph); 127.89 (d, Ph); 172.59 (d, Ph); 127.53 (d, Ph); 127.47 (d, Ph); 127.33 (d, Ph); 117.32 (d, Cp); 109.42 (d, C(2); 97.88 (s, C(Ph)$_2$O); 97.27 (s, C(Ph)$_2$O); 83.83 (d, C(4) oder C(5)); 80.30 (d, C(5) or C(4)); 35.51 (s, $\underline{C}$(CH$_3$)$_3$); 24.74 (q, C($\underline{CH_3}$)$_3$.

Subsidiary Isomer $^1$H-NMR spectrum ($CD_2Cl_2$, 400 MHz); 7.20–7.70 (m, 20H, Ph); 6.56 (s, 5H, Cp); 5.03 (d, J=7.5, 1H, H-C(4) or H-C(5)); 4.78 (d, J=7.5, 1H, H-(C5) or H-C(4); 3.44 (s, 1H, H-C(2)); 0.61 (s, 9H, C($\underline{CH_3}$)$_3$).

$^{13}$C-NMR spectrum ($CD_2Cl_2$, 100 MHz): 146.49 (s, Ph); 146.45 (s, Ph); 142.53 (s, Ph); 142.06 (s, Ph); 129.25 (d, Ph); 128.84 (d, Ph); 128.63 (d, Ph); 128.53 (d, Ph); 128.16 (d, Ph); 128.07 (d, Ph); 127.99 (d, Ph); 127.92 (d, Ph); 127.88 (d, Ph); 127.55 (d, Ph); 127.46 (d, Ph); 127.17 (d, Ph); 117.80 (d, Cp); 109.85 (d, C(2); 97.52 (s, C(Ph)$_2$O); 97.40 (s, C(Ph)$_2$O); 80.83 (d, C(4) or C(5)); 80.01 (d, C(5) or C(4)); 35.30 (s, $\underline{C}$(CH$_3$)$_3$); 24.38 (q, C($\underline{CH_3}$)$_3$.

b)

[(4S,5S)-2-(t-Butyl)-1,3-dioxolane-4,5-bis-(diphenylmethoxy)]-cyclopentadienylallyltitanium The reaction solution obtained in a) is cooled to 0° C. and 1.8 ml (2.25 mmol) of allymagnesium chloride (1.25-molar solution in tetrahydrofuran) are added dropwise in the course of 5 minutes. The yellow-brown suspension is stirred for 1 hour at 0° C. The reaction solution thus obtained is used for the next stage without further treatment.

Example 2 a)

[(4R,5R)-2,2-Dimethyl-1,3-dioxolane-4,5-bis-(diphenylmethoxy)]-cyclopentadienyltitanium chloride 1.17 g (2.5 mmol) of (4R,5R)-2,2-dimethyl-4,5-[bis-(diphenylhydroxymethyl)]-1,3-dioxolane are added to a solution of 0.55 g (2.5 mmol) of cyclopentadienyltitanium trichloride in 50 ml of diethyl ether. A solution of 0.56 g (5.5 mmol) of triethylamine in 10 ml of diethyl ether is added dropwise, in the course of 30 minutes and at room temperature (RT), to the above reaction solution. The pale yellow suspension is stirred at RT for a further 12 hours, and the triethylamine hydrochloride formed is filtered off with suction under argon and washed with three times 10 ml of ether. The reaction solution thus obtained is used for the next stage without further treatment.

$^1$H-NMR spectrum (CD$_2$Cl$_2$, 400 MHz): 7.65–7.27 (m, 20H, Ph); 6.43 (s, 5H, Cp); 5.16 (d, J=7.0, 1H, H-C(4) or H-C(5)); 4.95 (d, J=7.0, 1H, H-C(5) or H-C(4); 0.94 (s, 3H, CH$_3$); 0.50 (s, 3H, CH$_3$).

$^{13}$C-NMR spectrum (CD$_2$Cl$_2$, 100 MHz): 148.87 (s, Ph); 146.72 (s, Ph); 142.86 (s, Ph); 142.72 (s, Ph); 129.75 (d, Ph); 129.08 (d, Ph); 128.60 (d, Ph); 128.36 (d, Ph); 127.99 (d, Ph); 127.92 (d, Ph); 127.73 (d, Ph); 127.68 (d, Ph); 127.59 (d, Ph); 127.57 (d, Ph); 127.55 (d, Ph); 127.49 d, Ph); 117.48 (d, Cp); 111.71 (s, C(2)); 98.65 (s, C(Ph)$_2$O); 98.06 (s, C(Ph)$_2$O); 82.12 (d, C(4) or C(5)); 81.67 (d, C(5) or C(4)); 27.60 (q, (CH$_3$); 27.00 (q, (CH$_3$).

b)

[4R,5R)-2,2-Dimethyl-1,3-dioxolane-4,5-bis-(diphenylmethoxy)]-cyclopentadienylallyltitanium The reaction solution obtained in a) is cooled to 2° C. and 1.8 ml (2.25 mmol) of allylmagnesium chloride (1.25-molar solution in tetrahydrofuran) are added dropwise in the course of 5 minutes. The orange suspension is stirred for 1 hour at 2° C. and filtered with suction under argon. The reaction solution thus obtained is used for the next stage without further treatment.

$^1$H-NMR spectrum (CD$_2$Cl$_2$, 250 MHz): 7.65–7.27 (m, 20H, Ph); 6.15 (s, 5H, Cp); 5.85 (quint. J=11.5, H-C(2')) 5.40 (d, J=7.0, 1H, H-C(4) or H-C(5)); 4.78 (d, J=7.0, 1H, H-(C5) or H-C(4); 3.36 (d, J=11.5, 4H, H-C(1'), H-C(3')); 0.72 (s, 3H, CH$_3$); 0.58 (s, 3H, CH$_3$).

$^{13}$C-NMR spectrum (CD$_2$Cl$_2$, 62.9 MHz): 148.48 (s, Ph); 147.86 (s, Ph); 143.85 (s, Ph); 143.35 (d, C(2')); 143.23 (s, Ph); 129.75 (d, Ph); 129.08 (d, Ph); 128.60 (d, Ph); 128.36 (d, Ph); 127.99 (d, Ph); 127.92 (d, Ph); 127.73 (d, Ph); 127.68 (d, Ph); 127.59 (d, Ph); 127.57 (d, Ph); 127.55 (d, Ph); 127.49 (d, Ph); 115.25 (d, Cp); 112.10 (s, C(2)); 94.95 (s, C(Ph)$_2$O); 88.03 (t, C(1'), C(3')); 82.30 (d, C(4) or C(5)); 82.25 (d, C(5) or C(4)); 27.67 (q, (CH$_3$); 27.64 (q, (CH$_3$).

Example 3 a)

[(4S,5S)-2,2-Dimethyl-1,3-dioxolane-4,5-bis-(diphenylmethoxy)]-cyclopentadienyltitanium chloride is prepared as in Example 2a using (4S,5S)-2,2-dimethyl-4,5-[(bis-(diphenylhydroxymethyl)]-dioxolane as starting material b)

[(4S,5S)-2,2-Dimethyl-1,3-dioxolane-4,5-bis-(diphenylmethoxy)]-cyclopentadienylallyltitanium is prepared as in Example 2b, using as starting material [(4S,5S)-2,2-dimethyl-1,3-dioxolane-4,5-bis-(diphenylmethoxy)]-cyclopentadienyltitanium chloride Example 4 a)

[(4R,5R)-2,2-Dimethyl-1,3-dioxolane-4,5-bis-(diphenylmethoxy)]-cyclopentadienyl-E-crotyltitanium 10 ml (10 mmol) of (crotyl)MgCl (1-molar solution in diethyl ether) are added at −10° C. to 10 mmol of [(4R,5R)-2,2-dimethyl-1,3-dioxolane-4,5-bis-(diphenylmethoxy)]-cyclopentadiethyltitanium chloride, prepared analogously to Example 2a, in 160 ml of diethyl ether. The rust-red suspension is stirred for 2 hours at this temperature and filtered under argon. The reaction solution thus obtained can be concentrated or used for the next stage without further treatment.

$^1$H-NMR spectrum (CD$_2$Cl$_2$, 250 MHz): 7.65–7.15 (m, 20H, Ph); 6.08 (s, 5H, Cp); 5.46 (dxtxq, J=14.0, 8.5, 1.5, H-C(2')); 4.82 (dxq, J=14.0, 6.5, H-C(3')); 5.11 (d, J=7.0, 1H, H-C(4) or H-C(5)); 4.47 (d, J=7.0, 1H, H-(C5) or H-C(4); 2.26 (dxd, J=8.5, 8.5 H-C(1')); 2.17 (dxd, J=8.5, 8.5 H-C(1')); 1.67 (dxd, 3H, J=6.5, 1.5, H-(C4')); 0.68 (s, 3H, C(2)-CH$_3$); 0.58 (s, 3H, C(2)-CH$_3$).

Example 5 a)

(4R,5R)-2,2-Dimethyl-4,5-[bis-(dipentafluorophenylhydroxymethyl)]-1,3-dioxolane 6.25 ml (10 mmol) of n-butylLi in hexane are added dropwise, in the course of 45 minutes and at −78° C., to a solution of 1.25 ml (10 mmol) of bromopentafluorobenzene in 30 ml of diethyl ether and the mixture is warmed to room temperature (RT), stirred and cooled to 0° C. Diethyl (4R,5R)-2,2-dimethyl-1,3-dioxolane-4,5-dicarboxylate (10 mmol), dissolved in 20 ml of diethyl ether is added dropwise slowly to the above reaction solution, and the mixture is stirred for 12 hours at RT and hydrolysed by adding a saturated solution of NH$_4$Cl slowly. The emulsion is extracted with 3 × 80 ml of diethyl ether, and the extract is washed with a saturated solution of NaCl, dried over Na$_2$SO$_4$ and evaporated. The product is purified by flash chromatography (80 g of SiO$_2$, 1:5 ether/hexane). Yield: 4.63 g (56%).

$^1$H-NMR-Spectrum (CDCl$_3$, 250 MHz): 5.43 (s, 2H); 4.95 (s, 2H); 1.40 (s, 6H).

b)

[(4R,5R)-2,2-Dimethyl-1,3-dioxolane-4,5-bis-(dipentafluorophenylmethoxy)]-cyclopentadienyltitanium chloride Prepared analogously to Example 2a, but using (4R,5R)-2,2-dimethyl-4,5-[bis-(dipentafluorophenylhydroxymethyl)]-1,3-dioxolane as starting material.

c)
[(4R,5R)-2,2-Dimethyl-1,3-dioxolane-4,5-bis-(dipentafluorophenylmethoxy)]-cyclopentadienylallyltitanium The reaction solution obtained in Example 5b is reacted analogously to Example 2b and can be used for the next stage without further processing.

Example 6 a)
(4R,5R)-2,2-Dimethyl-4,5-[bis-(di-2-furylhydroxymethyl)]-1,3-dioxolane

A solution of 97 ml of n-butylLi (155 mmol) in hexane is diluted with 100 ml of diethyl ether and cooled to −20° C., and 11.62 ml (160 mmol) of furane are added in the course of 10 minutes. The reaction solution is warmed slowly to RT and is then heated under reflux for 4 hours. 9.84 g (40 mmol) of diethyl (4R,5R)-2,2-dimethyl-1,3-dioxolane-4,5-dicarboxylate, dissolved in 20 ml of ether, are added slowly with ice cooling to the above reaction solution, and the mixture is then stirred for 2 hours at RT and for 16 hours under reflux and hydrolysed by adding 300 ml of saturated $NH_4Cl$ solution slowly. The emulsion is filtered through Hyflo and extracted with 3× 200 ml of diethyl ether, and the extracts are washed with saturated NaCl solution, dried over $Na_2SO_4$ and evaporated. The product is purified by flash chromatography (800 g of $SiO_2$, 10:1 toluene/ether). Yield: 5.10 g (30%).

$^1$H-NMR spectrum (CDCl$_3$, 250 MHz): 7.48–7.36 (m, 4H); 6.48–6.30 (m, 8H); 4.78 (s, 2H); 1.02 (s, 6H).

$^{13}$C-NMR spectrum (CDCl$_3$, 62.9 MHz): 154.3 (s), 152.9 (s), 142.4 (d); 111.5 (s); 110.6 (d); 110.3 (d); 109.8 (d), 109.3 (d); 80.4 (d); 72.6 (s); 26.7 (q).

b)
[(4R,5R)-2,2-Dimethyl-1,3-dioxolane-4,5-bis(di-2-furyl-methoxy)]-cyclopentadienyltitanium chloride Prepared analogously to Example 2a, but using (4R,5R)-2,2-dimethyl-4,5-[bis-(di-2-furylhydroxymethyl)]-1,3-dioxolane as starting material.

c)
[(4R,5R)-2,2-Dimethyl-1,3-dioxolane-4,5-bis(di-2-furyl-methoxy)]-cyclopentadienylallyltitanium The reaction solution obtained in Example 6b is reacted analogously to Example 2b and can be used for the next stage without further treatment.

Example 7 a)
(4R,5R)-2,2-Dimethyl-4,5-[bis-(di-2-propenylhydroxymethyl)]-1,3-dioxolane 13.8 g (575 mmol) of Mg turnings in 50 ml of tetrahydrofuran (THF) are initially taken and 43.7 ml (500 mmol) of 2-bromopropene are added dropwise in the course of 1.5 hours, and the mixture is heated under reflux for 1 hour and cooled to 40° C. 24.6 g (100 mmol) of diethyl (4R,5R)-2,2-dimethyl-1,3-dioxolane-4,5-dicarboxylate, dissolved in 50 ml of THF, are added dropwise to the reaction solution in the course of 1 hour. The mixture is then hydrolysed with 250 ml of 2N $H_2SO_4$, the phases are separated, the aqueous phase is extracted with 3× 200 ml of diethyl ether, and the combined ethereal phases are washed twice with saturated NaCl solution, dried over $Na_2SO_4$ and evaporated. The product is purified by flash chromatography (1 kg of $SiO_2$, 1:5 ether/hexane). Yield: 6.1 g (18.9%).

$^1$H-NMR spectrum (CDCl$_3$, 250 MHz): 5.25 (dxq, J=1.5, 0.5, 2H); 5.19 (dxq, J=1.5, 0.5, 2H); 5.11 (dxq, J=1.5, 1.5, 2H); 5.00 (dxq, J=1.5, 1.5, 2H); 4.40 (s, 2H); 1.80 (dxd, J=1.5, 0.5, 6H) 1.72 (dxd J=1.5, 0.5, 6H); 1.40 (s, 6H).

$^{13}$C-NMR spectrum (CDCl$_3$, 62.9 MHz): 146.1 (s); 145.7 (s); 114.3 (t); 113.7 (t); 98.4 (s); 80.2 (d); 79.1 (s); 27.2 (q); 21.0 (q); 19.4 (q).

b)
[(4R,5R)-2,2-Dimethyl-1,3-dioxolane-4,5-bis-(di-2-propenyl-methoxy)]-cyclopentadienyltitanium chloride Prepared analogous to Example 2a, using (4R,5R)-2,2-dimethyl-4,5-[bis-(di-2-propenylhydroxymethyl)]-1,3-dioxolane as starting material.

c)
[(4R,5R)-2,2-Dimethyl-1,3-dioxolane-4,5-bis-(di-2-propenyl-methoxy)]-cyclopentadienylallyltitanium The reaction solution obtained in Example 7b is reacted analogously to Example 2b and can be used for the next stage without further treatment.

Example 8

[(4R,5R)-2,2-Diphenyl-1,3-dioxolane-4,5-bis(diphenylmethoxy)]-cyclopentadienyltitanium chloride Prepared analogously to Example 2a, using (4R,5R)-2,2-diphenyl-4,5-[bis-(diphenylhydroxymethyl)]-1,3-dioxolane as starting material.

$^1$H-NMR spectrum (CDCl$_3$, 250 MHz): 7.70–6.40 (m, 30H, Ph); 6.29 (s, 5H, Cp); 5.33 (d, J=7.0, 1H, H-C(4) or H-C(5)); 5.20 (d, J=7.0, 1H, H-(C5) or H-C(4);

$^{13}$C-NMR spectrum (CDCl$_3$, 62.89 MHz): 146.4 (s, Ph); 146.3 (s, Ph); 144.0 (s, Ph); 143.4 (s, Ph); 141.3 (s, Ph); 140.2 (s, Ph); 128.6–126.3 (d, 16C, Ph); 125.4 (d, Ph); 125.2 (d, Ph); 116.8 (d, Cp); 112.2 (s, C(2); 98.4 (s, C(Ph)$_2$O); 97.8 (s, C(Ph)$_2$O); 84.3 (d, C(4) or C(5)); 83.5 (d, C(5) or C(4)).

Example 9 a)
[(4R,5R)-2,2-Dimethyl-1,3-dioxolane-4,5-bis(diphenylmethoxy)]-pentamethylcyclopentadienylzirconium chloride 9.32 g (20 mmol) of (4R,5R)-2,2-dimethyl-4,5-[bis-(diphenylhydroxymethyl)]-1,3-dioxolane are added to a solution of 6.66 g (20 mmol) of pentamethylcyclopentadienylzirconium trichloride in 150 ml of diethyl ether. A solution of 6.1 ml (44 mmol) of triethylamine in 50 ml of diethyl ether is added dropwise, in the course of 30 minutes and at room temperature (RT), to the above reaction solution. The beige suspension is stirred at RT for a further 12 hours, and the triethylamine hydrochloride formed is filtered off with suction under argon and washed with three times approx. 20 ml of diethyl ether. The reaction solution thus obtained can be used in the next stage without further treatment.

$^1$H-NMR spectrum (CDCl$_3$, 250 MHz): 7.55–7.18 (m, 20H, Ph); 5.12 (d, J=7.0, 1H, H-C(4) or H-C(5)); 4.92 (d, J=7.0, 1H, H-(C5) or H-C(4); 1.95 (s, 15H, Cp*); 0.46 (s, 3H, CH$_3$); 0.45 (s, 3H, CH$_3$).

$^{13}$C-NMR spectrum (CDCl$_3$, 62.89 MHz): 148.5 (s, Ph); 148.2 (s, Ph); 143.6 (s, Ph); 143.4 (s, Ph); 129.8 (d, Ph); 129.5 (d, Ph); 128.6–127.5 (d, 10C, Ph); 123.74 (s, Cp*); 111.62 (s, C(2); 91.38 (s, C(Ph)$_2$O); 90.19 (s, C(Ph)$_2$O); 82.16 (d, C(4) or C(5)); 80.55 (d, C(5) or C(4)); 27.50 (q, (CH$_3$); 27.40 (q, (CH$_3$); 11.10 (q, Cp*).

Ph: phenyl.

Cp*: cyclopentadienyl.

b)

[(4R,5R)-2,2-Dimethyl-1,3-dioxolane-4,5-bis(diphenylmethoxy)]pentamethylcyclopentadienylmethylzirconium A solution of 5 mmol of the zirconium compound of Example 9a in 60 ml of diethyl ether is cooled to −74° C., 1.5 ml of a 3-molar solution of CH$_3$MgBr in THF is added and the mixture is stirred for 2 hours at −74° C. The reaction solution thus obtained is used for the next stage without further treatment.

Example 10 a)

[(4R,5R)-2,2-Dimethyl-1,3-dioxolane-4,5-bis(diphenylmethoxy)]pentamethylcyclopentadienylhafnium chloride Prepared analogously to Example 9a, but using pentamethylcyclopentadienylhafnium trichloride as starting material.

$^1$H-NMR spectrum (CDCl$_3$, 250 MHz): 7.55–7.2 (m, 20H, Ph); 5.08 (d, J=7.0, 1H, H-C(4) or H-C(5)); 4.92 (d, J=7.0, 1H, H-(C5) or H-C(4); 2.00 (s, 15H, Cp*); 0.46 (s, 3H, CH$_3$); 0.43 (s, 3H, CH$_3$).

$^{13}$C-NMR spectrum (CDCl$_3$, 62.89 MHz): 148.63 (s, Ph); 148.18 (s, Ph); 143.84 (s, Ph); 143.70 (s, Ph); 129.8 (d, Ph); 129.1 (d, Ph); 128.6–127.5 (d, 10C, Ph); 122.14 (s, Cp*); 112.01 (s, C(2)); 90.34 (s, C(Ph)$_2$O); 90.19 (s, C(Ph)$_2$O); 82.17 (d, C(4) or C(5)); 80.58 (d, C(5) or C(4)); 27.56 (q, (CH$_3$); 27.40 (q, (CH$_3$); 10.87 (q, Cp*).

b)

[(4R,5R)-2,2-Dimethyl-1,3-dioxolane-4,5-bis(diphenylmethoxy)]pentamethylcyclopentadienylmethylhafnium Prepared analogously to Example 9b, but using the hafnium compound of Example 10a as starting material.

B) USE EXAMPLES

Example 11

Preparation of (S)-1-phenyl-3-buten-1-ol

A solution of 1.25 mmol of the titanium compound of Example 2b in 60 ml of diethyl ether is cooled to −74° C., and 0.1 ml (1.0 mmol) of freshly distilled benzaldehyde is added. The slightly yellow, clear solution is stirred for a further 2 hours at −74° C. and 5 ml of a 5N H$_2$O/THF solution are added and the mixture is warmed to RT, stirred for a further hour at this temperature, filtered with suction and concentrated on a rotary evaporator. The crude product (0.80 g of a clear colourless oil) is flash-chromatographed (60 g of silica gel, 35 cm long, cross-section 2 cm, 5 ml/fraction, 0.4 bar, 10:1 toluene/ethanol). 0.098 g of product is obtained. Yield: 66%, ee: 93%.

Example 12

Preparation of (S)-1-tridecen-4-ol

A solution of 1.25 mmol of the titanium compound of Example 2b in 60 ml of diethyl ether is cooled to −74° C. and 0.19 ml (0.1 mmol) of freshly distilled capraldehyde is added. The slightly yellow, clear solution is stirred for a further 2 hours at −74° C. and 5 ml of a 5N H$_2$O/THF solution are added and the mixture is warmed to RT, stirred for a further hour at this temperature, filtered with suction and evaporated on a rotary evaporator. The crude product (1.13 g of clear, colourless oil) is flash-chromatographed (60 g of silica gel, 35 cm long, cross-section 2 cm, 5 ml/fraction, 0.4 bar, 10:1 toluene/ethanol) and is then distilled in a bulb tube (b.p.: ≈120–130 at 0.104 mbar). 0.141 g of product is obtained. Yield: 71%, ee: 95%.

Example 13

Preparation of (R)-1-phenyl-3-buten-1-ol

A solution of 2.25 mmol of the titanium compound of Example 1b in 120 ml of diethyl ether is cooled to −74° C. and 0.2 ml (2.0 mmol) of freshly distilled benzaldehyde is added. The beige suspension is stirred for a further 2 hours at −74° C. and 5 ml of a 5N H$_2$O/THF solution are added. The beige suspension is warmed to RT, stirred for a further hour at this temperature, filtered with suction and concentrated on a rotary evaporator. The crude product (1.53 g of yellow-brown oil) is flash-chromatographed twice (80 g of silica gel, 25 cm long, cross-section 2 cm, 10 ml/fraction, 0.5 bar, 20:1 toluene/ethanol); (50 g of silica gel, 25 cm long, cross-section 2 cm, 15 ml/fraction, 0.5 bar, 15:1 toluene/ethanol). 0.2 g of product are obtained. Yield: 66%, ee: 82%.

Example 14

Preparation of ethyl (2S,3R)-2-(tert-butoxycarbonylamino)-3-hydroxyhexanoate 7.6 ml of a 1.6M solution of butyllithium in hexane are added at −20° to −30° C. to a solution of 1.9 g of cyclohexylisopropylamine in 60 ml of tetrahydrofuran. After 20 minutes the mixture is cooled to −78° C. and a solution of 3.0 g of ethyl 1,1,3,3-tetramethyl-1,3-disilaazolidine-N-acetate in 60 ml of tetrahydrofuran is added dropwise. After stirring for 1 hour at −78° C., 161 ml of a 0.083M solution of [(4R,5R)-2,2-dimethyl-1,3-dioxolane-4,5-bis(diphenylmethoxy)]cyclopentadienyltitanium chloride (according to Example 2a) in ether are added dropwise. The solution is stirred for 43 hours at −78° C. and is then added via a steel cannula to a solution, cooled to −78° C., of 0.97 g of butyraldehyde in 15 ml of tetrahydrofuran. After stirring for 22 hours at −78° C., 1.5 ml of water are added and the mixture is warmed to room temperature and filtered. 24 ml of water and 4.8 ml of acetic acid are added to the filtrate and the mixture is stirred for 2 hours at room temperature and evaporated in vacuo. A sample (5 mg) of the residue is made into a derivative by treatment with trifluoroacetic anhydride in methylene chloride for 2 hours and is analysed by capillary gas chromatography (Chirasil-Val, 90°–180° C./2° C. per minute). According to this, the sample consists of 90.8% of the (2S,3R)-isomer (retention time 11.7 minutes) and 9.2% of the (2R,3S)-isomer (retention time 10.8 minutes). 250 ml of ether are added to the remainder of the crude product and the mixture is shaken with three times 100 ml of 0.1N hydrochloric acid. The aqueous phase is extracted with twice 250 ml of ether, adjusted to pH 4 with sodium hydroxide solution and concentrated to 50 ml in vacuo at room temperature. After 80 ml of dioxane, 6.7 g of sodium bicarbonate and 5.3 g of di-tert-butyl dicarbonate have been added, the mixture is stirred for 15 hours at room temperature. The reaction mixture is diluted with 250 ml of diethyl ether and washed with twice 250 ml of water and with saturated sodium chloride solution, and the aqueous phases are extracted with twice 250 ml of ether. The organic extracts are dried (Na$_2$SO$_4$) and evaporated. Chromatographing the residue (silica gel, 1:4 to 1:2 ethyl acetate/hexane) gives 2.09 g of ethyl (2S,3R)-tert-butoxycarbonylamino-3-hydroxyhexanoate.

Example 15

Preparation of (4R,1'S)-2,2-dimethyl-1,3-dioxolane-4-(1'-hydroxy-3'-buten-1'-yl)

A solution of 4.5 mmol of the titanium compound of Example 2b in 70 ml of diethyl ether is cooled to −74° C. and 0.52 g (4.0 mmol) of freshly distilled 2,3-O-isopropylidene-D-glyceraldehyde is added. The orange-yellow suspension is stirred for a further 4 hours at −74° C., 30 ml of a 45% aqueous ammonium fluoride solution are added and the mixture is warmed to room temperature, stirred overnight at this temperature and filtered with suction through Hyflo. The emulsion is diluted with 50 ml of diethyl ether and the organic phase is then separated off, washed and dried over Na$_2$SO$_4$. The crude product (2.5 g of a clear, yellowish oil) is suspended in 10 ml of pentane, and the suspension is stirred for 1 hour at room temperature and filtered with suction. The filtrate is flash-chromatographed (60 g of silica gel, 20 cm long, cross-section 2 cm, 30 ml/fraction, 0.4 bar, 1:2 diethyl ether/pentane). Yield: 0.2 g, ee >95%.

Example 16

Preparation of (4R,1'R)-2,2-dimethyl-1,3-dioxolane-4-(1'-hydroxy-3'-buten-1'-yl)

Preparation is carried out as in Example 8, but using the titanium compound of Example 3b. Yield: 0.26 g, ee >95%.

Example 17

Preparation of (R)-3-hydroxy-5-methylhexanoic acid 4.4 ml of 1.6M butyllithium in hexane are added under argon and at −25° C. to a solution of 1.12 ml of diisopropylamine in 15 ml of anhydrous diethyl ether (ether). After 25 minutes at −20° C., the mixture is cooled to −78° C. and 805 µl of tert-butyl acetate are added dropwise in the course of 10 minutes by means of a syringe. After stirring for 45 minutes at −78° C., a freshly prepared solution, precooled to −78° C., of 4.9 g of [(4R,5R)-2,2-dimethyl-1,3-dioxolane-4,5-bis-(diphenylmethoxy)]-cyclopentadienyltitanium chloride (according to Example 2a) in approx. 100 ml of ether is added via a cannula in the course of 15 minutes. The mixture is stirred for 30 minutes at −78° C. and for 3 hours at −30° C. and cooled to −78° C. and 650 µl of isovaleraldehyde are added by means of a syringe in the course of 5 minutes. After 2 hours at −78° C., 20 ml of 45% NH$_4$F solution are added and the mixture is warmed to room temperature. After stirring for 17 hours it is filtered, 10 ml of saturated sodium chloride solution are added to the filtrate and the mixture is extracted with three times 100 ml of ether. The organic phases are washed with saturated NaCl solution and 1N HCl, dried (MgSO$_4$) and evaporated. The residue (5.1 g) is stirred in 6 ml of 2N sodium hydroxide solution and 12 ml of methanol for 2 hours at 50° C. After the methanol has been removed by evaporation in vacuo, the residue is extracted with three times 50 ml of ether. The aqueous phase is acidified with concentrated hydrochloric acid and extracted with three times 100 ml of ethyl acetate. The ethyl acetate phases are washed with twice 50 ml of saturated sodium chloride solution, dried (MgSO$_4$) and evaporated. The residue, 835 mg of 1-(R)-3-hydroxy-5-methylhexanoic acid of 78% optical purity, is recrystallized twice from cyclohexane (60 ml and 150 ml). Yield: 595 mg of product of 96% optical purity, melting point 86° C.; $[\alpha]_D = -14.7°$ (c=1, CHCl$_3$). (+)-(R)-Ipsenol can be prepared from this by the instructions in EP-A 0,254,685 (Example 41d to 41g).

Example 18

Preparation of (S)-1-phenyl-3-buten-1-ol

Analogous to Example 11, but [(4R,5R)-2,2-dimethyl-1,3-dioxolane-4,5-bis-(dipentafluorophenylmethoxy)]-cyclopentadienylallyltitanium (prepared as in Example 5c) is used as the starting material. Yield: 62%, (ee: 53.7%).

Example 19

Preparation of (S)-1-phenyl-3-buten-1-ol

Analogous to Example 11, but [(4R,5R)-2,2-dimethyl-1,3-dioxolane-4,5-bis-(di-2-furylmethoxy)]-cyclopentadienyltitanium chloride (prepared as in Example 6c) is used as the starting material. Yield: 63%, (ee: 65.5%).

Example 20

Preparation of (S)-1-phenyl-3-buten-1-ol

Analogous to Example 11, but [(4R,5R)-2,2-dimethyl-1,3-dioxolane-4,5-bis-(di-2-propenylmethoxy)]-cyclopentadienyltitanium chloride (prepared as in Example 7c) is used as the starting material. Yield: 53%, (ee: 71.3%).

Example 21

Preparation of tert-butyl (4S,1'S)-2,2-dimethyl-4-(1'-hydroxy-3'-butenyl)-oxazolidine-3-carboxylate 65 ml of a solution (4.5 mmol) of [(4R,5R)-2,2-dimethyl-1,3-dioxolane-4,5-bis-(diphenylmethoxy)]-cyclopentadienylallyltitanium (prepared as in Example 2b) is cooled to −74° C. and 917 mg (4 mmol) of tert-butyl (4S)-2,2-dimethyl-4-formyloxazolidine-3-carboxylate dissolved in 5 ml of diethyl ether is added dropwise. The slightly yellow, clear solution is stirred for a further 3 hours at −74° C., 25 ml of a 45% aqueous solution of NH$_4$F are added and the mixture is warmed to RT, stirred for a further 12 hours at this temperature (white precipitate) and filtered through Celite. The aqueous phase is separated off and extracted with 100 ml of diethyl ether. The organic phase is washed with twice 50 ml of saturated NaCl solution, dried with MgSO$_4$ and evaporated. The product is purified by being subjected twice to flash chromatography (220 g of SiO$_2$, 2.5:1 hexane/ethyl acetate) or (20 g of SiO$_2$, 2.5:1 hexane/ethyl acetate). Yield: 1.007 g, 93%, de (ee) 95%, $[\alpha]_D^{Rt} = -17.0°$ (c=0.95, C$_6$H$_6$).

$^{13}$C-NMR (C$_6$D$_6$, 62.9 MHz, 340K) 24.1 (CH$_3$); 27.0 (CH$_3$); 28.4 (C(CH$_3$)$_3$; 36.1 (C(2')); 61.9 (C(4)); 64.6 (C(5)); 72.3 (C(1')); 80.4 (C(CH$_3$)$_3$; 94.3 (C(2)); 117.0 (C(4')); 135.7 (d, C(3')); 153.8 (COO-t-Bu).

$^1$H-NMR (C$_6$D$_6$, 250 MHz, 340K): 1.39 (s, C(CH$_3$)$_3$), 1.45 (s, CH$_3$); 1.62 (s, CH$_3$); 2.10 (dxdxdxdxd, 1H, J=14.0, 7.0, 7.0, 1.0, 1.0, H-C(2'); 2.30 (dxdxdxdxd, 1H, J=14.0, 6.5, 3.0, 1.0, 1.0, H-C(2'); 3.59–3.73 (m, 2H, H-C(5)); 3.84–3.96 (m, H-C(4), H-C(1')); 4.97–5.08 (m, 2H, H-C(4')); 5.92 (dxdxdxd J=17.0, 10.0, 7.0, 6.5, H-C(3')).

Example 22

Tert-butyl (4S,1'R)-2,2-dimethyl-4-(1'-hydroxy-3'-butenyl)-oxazolidine-3-carboxylate Prepared analogously to Example 21, but using [(4S,5S)-2,2-dimethyl-1,3-dioxolane-4,5-bis-(diphenylmethoxy)]-cyclopentadienylallyltitanium (Example 3b). Yield: 1.037 g, 95%, de (ee) 99%, $[\alpha]_D^{Rt} = +4.4°$ (c=0.985, $C_6H_6$).

$^1$H-NMR ($C_6D_6$, 250 MHz, 340K): 1.39 (s, C(CH$_3$)$_3$), 1.46 (s, CH$_3$); 1.62 (s, CH$_3$); 2.16–2.23 (m, 2H, H-C(2'); 3.63 (dxd, 1H, 9.0, 6.5, H-C(5)); 3.80–3.92 (m, 3H, H-C(1'), H-C(4), H-C(5)); 4.97–5.12 (m, 2H, H-C(4')); 5.90 (dxdxdxd J=17.0, 10.0, 6.50, 6.5, H-C(3')).

$^{13}$C-NMR ($C_6D_6$, 62.9 MHz, 340K) 24.2 (q, CH$_3$); 27.0 (q, CH$_3$); 28.4 (q, t-Bu); 38.9 (t, C(2')); 62.0 (d, C(4)); 64.5 (t, C(5)); 72.0 (d, C(1')); 80.1 (s, t-Bu); 94.4 (s, C(2)); 116.9 (t, C(4')); 135.9 (d, C(3')); 153.8 (s)).

Example 23

Preparation of ethyl (2S,3R)-2-(tert-butoxycarbonylamino)-3-hydroxyhexanoate 7.6 ml of a 1.6M solution of butyllithium in hexane are added at −20° to −30° C. to a solution of 1.9 g of cyclohexylisopropylamine in 60 ml of tetrahydrofuran. After 20 minutes the mixture is cooled to −78° C., and a solution of 3.0 g of ethyl 1,1,3,3-tetramethyl-1,3-disilaazolidine-N-acetate in 60 ml of tetrahydrofuran is added.

After stirring for 1 hour at −78° C., 161 ml of a 0.083M solution of [(4R,5R)-2,2-dimethyl-1,3-dioxolane-4,5-bis-(diphenylmethoxy)]-cyclopentadienyltitanium chloride (according to Example 2a) in diethyl ether are added dropwise. The solution is stirred for 43 hours at −78° C. and is then added via a steel cannula to a solution, cooled to −78° C., of 0.97 g of butyraldehyde in 15 ml of tetrahydrofuran. After stirring for 22 hours at −78° C., 1.5 ml of water are added and the mixture is warmed to room temperature and filtered. 24 ml of water and 4.8 ml of acetic acid are added to the filtrate, which is stirred for 2 hours at room temperature and evaporated in vacuo under mild conditions. A sample (5 mg) of the residue is reacted for 2 hours with trifluoroacetic anhydride in methylene chloride and analysed by capillary gas chromatography (Chirasil-Val, 90°–180° C./2° C. per minute). According to this, the sample consists of 90.8% of the (2S,3R)-isomer (retention time 11.7 minutes) and 9.2% of the (2R,3S)-isomer (retention time 10.8 minutes). 250 ml of diethyl ether are added to the remainder of the crude product and the mixture is shaken with three times 100 ml of 0.1N hydrochloric acid. The aqueous phase is extracted with twice 250 ml of diethyl ether, adjusted to pH 4 with sodium hydroxide solution and concentrated to about 50 ml in vacuo at room temperature. After 80 ml of dioxane, 6.7 g of sodium bicarbonate and 5.3 g of di-tert-butyl dicarbonate have been added the mixture is stirred for 15 hours at room temperature. The reaction mixture is diluted with 250 ml of diethyl ether and washed with twice 250 ml of water and saturated sodium chloride solution, and the aqueous phases are extracted with twice 250 ml of diethyl ether. The organic extracts are dried (Na$_2$SO$_4$) and evaporated. Chromatographing the residue (silica gel, 1:4 to 1:2 ethyl acetate/hexane) gives 2.09 g of ethyl (2S,3R)-tert-butoxycarbonylamino-3-hydroxyhexanoate.

Example 24

Preparation of tert-butyl (2S,3R)-2-(tert-butoxycarbonylamino)-3-hydroxyhexanoate a) tert-Butyl 1,1,3,3-tetramethyl-1,3-disilaazolidine-N-acetate 44.0 ml of triethylamine and a solution of 23.4 g of 1,2-bis-(chlorodimethylsilyl)-ethane in 100 ml of methylene dichloride are added slowly, with ice cooling and under an atmosphere of nitrogen, to a suspension of 14.0 g of tert-butyl glycine ester-hydrochloride in 200 ml of methylene dichloride. After stirring for 19 hours at room temperature, a further 7 ml of triethylamine and 5.4 g of 1,2-bis-(chlorodimethylsilyl)-ethane are added and stirring is continued for 22 hours. The reaction mixture is washed with a buffer solution (0.41M Na$_2$HPO$_4$ and 0.28M KH$_2$PO$_4$ in H$_2$O), H$_2$O and saturated sodium chloride solution; the aqueous phases are extracted twice with methylene dichloride. The organic phases are dried with Na$_2$SO$_4$ and evaporated, and the residue is distilled: 12.7 g of tert-butyl 1,1,3,3-tetramethyl-1,3-disilaazolidine-N-acetate (60°–63° C.; 0.02 mbar).

b) tert-Butyl (2S,3R)-2-(tert-butoxycarbonylamino)-3-hydroxyhexanoate 1.5 g of tert-butyl 1,1,3,3-tetramethyl-1,3-disilaazolidine-N-acetate in 30 ml of THF are added dropwise at −78° C. to a solution of lithium cyclohexylisopropylamide prepared analogously to Example 23 from 0.93 g of cyclohexylisopropylamine, 30 ml of THF and 3.8 ml of butyllithium (1.6M in hexane). After stirring for 1 hour at −78° C., 105 ml of a 0.063M solution of [(4R,5R)-2,2-dimethyl-1,3-dioxolane-4,5-bis-(diphenylmethoxy)cyclopentadienyltitanium chloride (according to Example 2a) in diethyl ether are added dropwise. The solution is stirred for 21 hours at −78° C. and is then added via a steel cannula to a solution cooled to −78° C., of 0.47 g of butyraldehyde in 10 ml of THF. After stirring for 23 hours at −78° C., 2.4 ml of acetic acid are added, the mixture is stirred for 15 minutes, 12 ml of water are added and the mixture is warmed to room temperature, stirred for 2 hours and evaporated under mild conditions. The residue is taken up in 0.1M HCl and the solution is extracted three times with diethyl ether. The organic phases are washed twice with 0.1N HCl. The pH of the combined aqueous phases is adjusted to 4 with 2N NaOH, the mixture is evaporated to a residual volume of about 50 ml, and 40 ml of dioxane, 3.36 g of NaHCO$_3$ and 2.39 g of di-tert-butyl dicarbonate are added to the residue. After being stirred for 18 hours the reaction mixture is diluted with diethyl ether and washed twice with water and saturated sodium chloride solution; the aqueous phases are extracted twice with diethyl ether. The organic extracts are dried (Na$_2$SO$_4$) and evaporated: 4.37 g of crude product. A sample (5 mg) of this is heated in 0.3 ml of anhydrous 2N HCl in ethanol for 2 hours at 100° and the mixture is evaporated, reacted for 2 hours with 0.2 ml of trifluoroacetic anhydride in 0.3 ml of methylene chloride and analysed by capillary gas chromatography (Chirasil-L-Val, 90°-180° C./2° C. per minute). According to this, the sample consists of 97.1% of the (2S,3R)-enantiomer (retention time 11.8 minutes) and 2.9% of the (2R,3S)-enantiomer (retention time 10.9 minutes). Chromatographing the remainder of the residue (silica gel; 1:5 ethyl acetate/hexane) affords 1.03 g of tert-butyl (2S,3R)-tert-butoxycarbonylamino-3-hydroxyhexanoate in the form of an oil ($[\alpha]_D = -10.4°$; c=1.3 in ethanol).

Example 25

Preparation of (1S,2S)-2-methyl-1-phenyl-3-buten-1-ol 0.4 g (0.64 mmol) of the titanium compound prepared as in Example 4 are dissolved in 40 ml of diethyl ether, the solution is cooled to $-74°$ C., 0.065 ml (0.65 mmol) of benzaldehyde are added and the mixture is stirred for 2 hours at $-74°$ C. The reaction solution is then solution is then hydrolysed with 20 ml of aqueous ammonium fluoride solution, stirred overnight at RT, filtered through Hyflo and extracted with 3×40 ml of diethyl ether and the extract is washed with saturated NaCl solution, dried over $Na_2SO_4$ and evaporated.

The product is purified by flash chromatography (60 g of $SiO_2$, 1:5 diethyl ether/hexane). Yield: 0.082 g (90%), ee=98%, de>97%.

Example 26

Preparation of (S)-1-phenylethanol

A solution of 5 mmol of the zirconium compound of Example 9b in 60 ml of diethyl ether is cooled to $-74°$ C., 0.4 ml (4 mmol) of benzaldehyde are added, the mixture is stirred for 4 hours at this temperature and 30 ml of aqueous 45% $NH_4F$ solution are then added. The beige suspension is warmed to RT, stirred for a further 12 hours and filtered with suction, and the filtrate is concentrated on a rotary evaporator. The crude product (0.81 g) is flash-chromatographed (80 g of silica gel, 25 cm long, cross-section 2 cm, 30 ml/fraction, 0.4 bar, 1:5 diethyl ether/hexane) and distilled in a bulb tube. 0.303 g of product are obtained. Yield: 62%, ee: 97%.

The same product is obtained if the corresponding hafnium compound of Example 10b is used instead of the zirconium compound. Yield: 60%, ee 97%.

What is claimed is:

1. A compound of the formula I

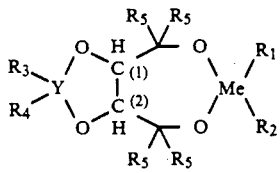

in which Me is tetravalent titanium, zirconium or hafnium, $R_1$ is linear or branched $C_1-C_{18}$alkyl, $C_2-C_{12}$alkenyl, $C_2-C_{12}$alkynyl or $C_3-C_8$cycloalkyl or $C_3-C_8$cycloalkenyl each of which is unsubstituted or substituted by $C_1-C_4$alkyl, or is $C_6-C_{12}$aryl, $C_7-C_{16}$alkaryl, $C_7-C_{16}$aralkyl, $C_8-C_{16}$alkaralkyl, $C_8-C_{16}$aralkenyl, $C_9-C_{16}$alkaralkenyl, $C_8-C_{16}$aralkynyl or $C_9-C_{16}$alkaralkynyl each of which is unsubstituted or monosubstituted or polysubstituted by $(C_6H_5)_2P-$, $(R_6O)_2P(O)-$, $(R_6)_3Si-$, $(R_6)_3SiO-$, $R_6SO_2-$, $-S-C_2-C_4$alkylene-S- or $-O-C_2-C_4$alkylene-O- in which $R_6$ is phenyl, benzyl or $C_1-C_8$alkyl, cyano, F, nitro, $C_1-C_{12}$alkylthio, $C_1-C_{12}$alkoxy, $-NR_{18}R_{19}$ wherein $R_{18}$ and $R_{19}$ are $C_1-C_{12}$alkyl, cyclopentyl, cyclohexyl, phenyl, benzyl, or $(R_6)_3Si-$, or $R_{18}$ and $R_{19}$ together are $C_3-C_6$alkylene, 3-oxapentylene or $-Si(R_6)_2C_2-C_3$alkylene-$Si(R_6)_2-$ or $COR_7$ in which $R_7$ is the radical of a monohydric alcohol; or $R_1$ is a radical of a $C_2-C_{20}$enol, $C_2-C_{20}$enamine or $C_2-C_{20}$enhydrazine which is linked via the O atom or N atom; $R_2$ is cyclopentadienyl or indenyl each of which is unsubstituted or substituted by $C_1-C_6$alkyl, $C_2-C_6$alkenyl, $C_1-C_6$alkoxy, $C_5-C_6$cycloalkyl, $C_6-C_{12}$aryl, $C_7-C_{13}$aralkyl, tri-$C_1-C_6$alkoxysilyl, tri-$C_1-C_6$alkylsilyl, $R_6SO_2-$ or halogen, Y is C, Si or $-Si-O-SiR_3R_4-$, $R_3$ and $R_4$ independently of one another are H, linear or branched $C_1-C_{18}$alkyl or $C_2-C_{12}$alkenyl or $C_5-C_6$cycloalkyl or $C_5-C_6$cycloalkenyl each of which is unsubstituted or substituted by $C_1-C_4$alkyl, or are phenyl, naphthyl, benzyl, $C_1-C_6$alkylphenyl or $C_1-C_6$alkylbenzyl, or $R_3$ and $R_4$ together are $C_nH_{2n}-$ in which n is 3 to 7 and which is unsubstituted or sustituted by $-CN$, $-F$, $-Cl$, $-Br$, nitro, $C_1-C_{12}$alkylthio or $C_1-C_{12}$alkoxy, R is $C_6-C_{10}$aryl, $C_5-$ or $C_6-$heteroaryl which contains a single heteroatom which is selected from the group comprising O, S and N, or $R_5$ is benzyl, naphthylmethyl or $C_5-C_6$heteroarylmethyl which contains a single heteroatom which is selected from the group comprising O, S and N which is unsubstituted or substituted by $C_1-C_{12}$alkyl, $C_1-C_{12}$alkoxy, $C_1-C_{12}$alkylthio, cyano, $-NR_{18}R_{19}$, $-CONR_{18}R_{19}$, fluorine, $C_6-C_{10}$aryl, $R_6SO_2-$, $C_1-C_{12}$alkoxymethyl, $C_1-C_{12}$alkylthiomethyl, $-CH_2NR_{18}R_{19}$ or $-CH_2CONR_{18}R_{19}$ wherein $R_{18}$ and $R_{19}$ are as defined above, or $R_5$ is $C_1-C_{12}$alkyl, $C_2-C_{12}$alkenyl, $C_2-C_{12}$alkynyl, $C_3-C_8$cycloalkyl or $C_3-C_8$cycloalkenyl, and C(1) and C(2) are chiral atoms, predominantly in the form of enantiomers or diastereomers.

2. A compound according to claim 1, in which $R_1$ is linear or branched $C_1-C_{12}$alkyl, $C_2-C_{12}$alkenyl, $C_2-C_{12}$alkynyl, cycloalkyl or cycloalkenyl each of which has 3 to 8 ring C atoms, $C_6-C_{12}$aryl, $C_7-C_{16}$alkaryl, $C_7-C_{16}$aralkyl, $C_8-C_{16}$alkaralkyl, $C_8-C_{16}$aralkenyl, $C_9-C_{16}$alkaralkenyl, $C_8-C_{16}$aralkynyl or $C_9-C_{16}$alkaralkynyl each of which is unsubstituted or monosubstituted or polysubstituted by secondary amino, cyano, nitro, $C_1-C_6$alkylthio, $C_1-C_6$alkoxy or $-COR_7$ in which $R_7$ is $C_1-C_{12}$alkoxy; or $R_1$ is a radical of an enol, enamine or enhydrazine which is attached via the enol oxygen atom or via the enamine nitrogen atom.

3. A compound according to claim 2, in which $R_1$ is linear or branched $C_1-C_6$alkyl, $C_2-C_6$alkenyl, $C_2-C_6$alkynyl, cycloalkyl or cycloalkenyl each of which has 3 to 6 ring C atoms, phenyl, ($C_1-C_{10}$alkyl)-phenyl, phenyl-($C_1-C_2$alkyl), ($C_1-C_8$alkyl)-phenyl-($C_1-C_2$alkyl), phenylvinyl, phenylethynyl or phenylpropargyl, ($C_1-C_8$alkyl)-phenylvinyl, ($C_1-C_8$alkyl)-phenylethynyl or ($C_1-C_7$alkyl)-phenylpropargyl each of which is unsubstituted or monosubstituted or polysubstituted by secondary amino, cyano, nitro, $C_1-C_6$alkoxy, $C_1-C_6$alkylthio or $-COR_7$ in which $R_7$ is $C_1-C_{12}$alkoxy; or $R_1$ is a radical of an enol, enamine or enhydrazine which has up to 20 C atoms and is attached via an enol oxygen atom or an enamine nitrogen atom.

4. A compound according to claim 2, in which $R_1$ is methyl, ethyl, vinyl, allyl, crotyl, ethynyl, propargyl, cyclopentyl, cyclohexyl, cyclopentenyl, cyclohexenyl, phenyl, methylphenyl, benzyl, 1-phenyleth-2-yl, methylbenzyl, phenylvinyl, methylphenylvinyl, phenylethynyl, phenylpropargyl, methylphenylethynyl, dimethylphenylethynyl or dimethylphenylpropargyl each of which is unsubstituted or monosubstituted or polysubstituted by secondary amino, cyano, nitro, $C_1$-$C_6$alkoxy, $C_1$-$C_6$alkylthio or —$COR_7$ in which $R_7$ is $C_1$-$C_{12}$alkoxy; or $R_1$ is a radical of an enol, enamine or enhydrazine which has 2 to 16 C atoms and is attached via the enol oxygen atom or via the enamino nitrogen atom.

5. A compound according to claim 1, in which $R_2$ is cyclopentadienyl or indenyl each of which is unsubstituted or substituted by $C_1$-$C_6$alkyl, $C_2$-$C_6$alkenyl, $C_1$-$C_6$alkoxy, cycloalkyl having 5 or 6 ring C atoms, phenyl, benzyl, trialkoxysilyl having 1 to 6 C atoms in the alkoxy groups, trialkylsilyl having 1 to 6 C atoms in the alkyl groups, F, Cl, Br or $R_6SO_2$— in which $R_6$ is phenyl, tolyl, benzyl or $C_1$-$C_6$alkyl.

6. A compound according to claim 5, in which $R_2$ is cyclopentadienyl which is unsubstituted or substituted by $C_1$-$C_6$alkyl or trimethylsilyl.

7. A compound according to claim 1, in which $R_3$ and $R_4$ independently of one another are H, $C_1$-$C_{12}$alkyl, $C_2$-$C_{12}$alkenyl, cycloalkyl or cycloalkenyl each of which has 5 or 6 ring C atoms and is unsubstituted or substituted by $C_1$-$C_{14}$alkyl, or are phenyl, naphthyl, benzyl, $C_1$-$C_6$alkylphenyl or $C_1$-$C_6$alkylbenzyl or $R_3$ and $R_4$ together are —$C_nH_{2n}$— in which n is 4 to 6 and which is unsubstituted or substituted by —CN, —F, —Cl, nitro, $C_1$-$C_6$alkylthio or $C_1$-$C_6$alkoxy.

8. A compound according to claim 7, in which $R_3$ and $R_4$ independently of one another are H; $C_1$-$C_6$alkyl, cyclopentyl or cyclohexyl each of which is unsubstituted or substituted by $C_1$-$C_4$alkyl, or are phenyl, benzyl, $C_1$-$C_6$alkylphenyl or $C_1$-$C_6$alkylbenzyl or $R_3$ and $R_4$ together are pentamethylene or tetramethylene.

9. A compound according to claim 1, in which $R_3$ is H and $R_4$ or $R_3$ and $R_4$ are other than H.

10. A compound according to claim 1, in which Y is C.

11. A compound according to claim 1, in which $R_5$ is $C_2$-$C_4$alkenyl, 2-furyl or $C_6$-$C_{10}$aryl each of which is unsubstituted or substituted by $C_1$-$C_6$alkyl or F.

12. A compound according to claim 11, in which the aryl is phenyl, methylphenyl, pentafluorophenyl or naphthyl.

13. A compound according to claim 11, in which $R_5$ is propenyl, phenyl, pentafluorophenyl, methylphenyl or furyl.

14. A compound according to claim 1, in which $R_1$ is linear or branched $C_1$-$C_4$alkyl, $C_2$-$C_6$alkenyl or cycloalkyl or cycloalkenyl each of which has 3 to 6 ring C atoms and is unsubstituted or substituted by $C_1$-$C_4$alkyl, or $R_1$ is phenyl, benzyl, $C_1$-$C_6$alkylphenyl or $C_1$-$C_6$alkylbenzyl each of which is unsubstituted or substituted by secondary amino, cyano, nitro, $C_1$-$C_6$alkoxy, $C_1$-$C_6$alkylthio or —$COR_7$ in which $R_7$ is $C_1$-$C_{12}$alkoxy, or $R_1$ is a radical of an enol, enamine or enhydrazine which has up to 12 C atoms and is attached via an enol oxygen atom or an enamino nitrogen atom, $R_2$ is cyclopentadienyl which is unsubstituted or substituted by $C_1$-$C_4$alkyl or trimethylsilyl, Y is C, $R_3$ is H or is as defined for $R_4$ and $R_4$ is $C_1$-$C_{12}$alkyl, phenyl, benzyl, cyclopentyl or cyclohexyl or $R_3$ and $R_4$ together are tetramethylene or pentamethylene, $R_5$ is $C_2$-$C_4$alkenyl, phenyl, pentafluorophenyl or furyl and Me is tetravalent titanium, zirconium or hafnium.

15. A compound according to claim 1, in which the C(1) and C(2) atoms in formula I have either the R,R-configuration or the S,S-configuration.

16. A compound according to claim 15, in which Y is a chiral C atom, in the form of the diastereomers.

17. A compound according to claim 1, in which $R_1$ is $C_1$-$C_4$alkyl, allyl or the radical of an ester-enolate which has 2 to 12 C atoms and can be substituted by secondary amino, $R_2$ is cyclopentadienyl which is unsubstituted or substituted by methyl or trimethylsilyl, $R_3$ is H or is as defined for $R_4$ and $R_4$ is $C_1$-$C_6$alkyl, $R_5$ is propenyl, phenyl, pentafluorophenyl or furyl and Me is tetravalent titanium, zirconium or hafnium and Y is C.

18. A compound of the formula II

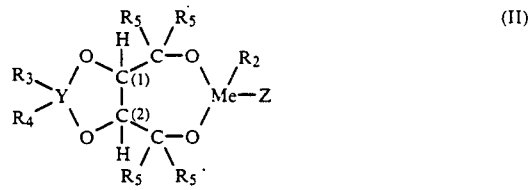

in which $R_2$, $R_3$, $R_4$, $R_5$, Y and Me are as defined in claim 1 and Z is an $PF_6^\ominus$, $SbF_6^\ominus$, $BF_4^\ominus$, $CF_3COO^\ominus$, sulfonate, $Cl^\ominus$ or $Br^\ominus$.

* * * * *